(12) United States Patent
Garcia Molina et al.

(10) Patent No.: US 11,141,093 B2
(45) Date of Patent: Oct. 12, 2021

(54) SYSTEM AND METHOD FOR DELIVERING SENSORY STIMULATION TO A USER TO ENHANCE A COGNITIVE DOMAIN IN THE USER

(71) Applicant: KONINKLIJKE PHILIPS N.V., Eindhoven (NL)

(72) Inventors: Gary Nelson Garcia Molina, Madison, WI (US); David White, Denver, CO (US); Birpal Singh Sachdev, Delmont, PA (US); William Gaussa, Jeannette, PA (US)

(73) Assignee: Koninklijke Philips N.V., Eindhoven (NL)

( * ) Notice: Subject to any disclaimer, the term of this patent is extended or adjusted under 35 U.S.C. 154(b) by 296 days.

(21) Appl. No.: 16/191,596

(22) Filed: Nov. 15, 2018

(65) Prior Publication Data

US 2019/0216353 A1 Jul. 18, 2019

Related U.S. Application Data

(60) Provisional application No. 62/588,670, filed on Nov. 20, 2017.

(51) Int. Cl.
*A61B 5/377* (2021.01)
*A61M 21/02* (2006.01)
(Continued)

(52) U.S. Cl.
CPC ............ *A61B 5/377* (2021.01); *A61B 5/0022* (2013.01); *A61B 5/369* (2021.01); *A61B 5/4812* (2013.01);
(Continued)

(58) Field of Classification Search
CPC .. A61M 21/00–02; A61M 2210/10–14; A61M 2230/04; A61B 5/0482–04847;
(Continued)

(56) References Cited

U.S. PATENT DOCUMENTS

2011/0015469 A1\* 1/2011 Walter .................... A61B 5/01
600/27
2014/0057232 A1 2/2014 Anderson
(Continued)

FOREIGN PATENT DOCUMENTS

WO 2014118650 A1 8/2014
WO 2015118415 A1 8/2015
(Continued)

OTHER PUBLICATIONS

Landsness, E. et al., "Sleep-dependent improvement in visuomotor learning: A causal role for slow waves", Sleep, vol. 32, No. 10, Oct. 2009.
(Continued)

*Primary Examiner* — Thaddeus B Cox

(57) ABSTRACT

The present disclosure pertains to a system configured to deliver sensory stimulation to a user to enhance a target cognitive domain during a sleep session. Example target cognitive domains include memory consolidation, vigilance, verbal fluency, sleepiness, and/or other target cognitive domains. The stimulation is adjusted based on the target cognitive domain to be enhanced. Responsive to one or more brain activity parameters indicating the user is in sufficiently deep sleep, the system is configured to cause one or more sensory stimulators to provide sensory stimulation to the user according to a stimulation strategy associated with the target cognitive domain. The system is configured to determine the effect of the sensory stimulation provided to the user using a quantification method associated with the stimulation strategy and the target cognitive domain. The
(Continued)

system includes one or more sensory stimulators, one or more sensors, one or more hardware processors, and/or other components.

12 Claims, 9 Drawing Sheets

(51) Int. Cl.
| | |
|---|---|
| *A61B 5/369* | (2021.01) |
| *A61N 5/06* | (2006.01) |
| *A61B 5/00* | (2006.01) |
| *A61M 21/00* | (2006.01) |
| *A61N 2/00* | (2006.01) |

(52) U.S. Cl.
CPC .......... *A61B 5/4836* (2013.01); *A61B 5/6868* (2013.01); *A61B 5/7235* (2013.01); *A61M 21/02* (2013.01); *A61M 2021/0011* (2013.01); *A61M 2021/0022* (2013.01); *A61M 2021/0027* (2013.01); *A61M 2021/0044* (2013.01); *A61M 2205/3584* (2013.01); *A61M 2205/3592* (2013.01); *A61M 2205/502* (2013.01); *A61M 2230/04* (2013.01); *A61M 2230/10* (2013.01); *A61M 2230/14* (2013.01); *A61M 2230/40* (2013.01); *A61M 2230/63* (2013.01); *A61N 2/006* (2013.01); *A61N 5/0618* (2013.01); *A61N 5/0622* (2013.01); *A61N 2005/0647* (2013.01)

(58) Field of Classification Search
CPC .......... A61B 5/4806–4815; A61B 5/369–386; A61B 5/398
See application file for complete search history.

(56) References Cited

U.S. PATENT DOCUMENTS

| | | | |
|---|---|---|---|
| 2016/0082222 A1 | 3/2016 | Garcia Molina et al. | |
| 2016/0151602 A1* | 6/2016 | Pan ..................... | A61B 5/7275 600/28 |
| 2017/0304587 A1* | 10/2017 | Santostasi .......... | A61B 5/04845 |
| 2017/0368348 A1* | 12/2017 | Le Van Quyen .. | A61N 1/36025 |

FOREIGN PATENT DOCUMENTS

| | | | |
|---|---|---|---|
| WO | 2016083929 A1 | 6/2016 | |
| WO | 2016102602 A1 | 6/2016 | |
| WO | WO-2016092515 A1 * | 6/2016 | .......... A61B 5/4812 |

OTHER PUBLICATIONS

H.-V. V Ngo, et al, "Driving Sleep Slow Oscillations by Auditory Closed-Loop Stimulation—A Self-Limiting Process," J. Neurosci., vol. 35, No. 17, pp. 6630-6638, 2015.

M. Bellesi, et al, "Enhancement of sleep slow waves: underlying mechanisms and practical consequences," Front. Syst. Neurosci., vol. 8, No. October, pp. 1-17, Oct. 2014.

N. A. Papalambros, et al, "Acoustic enhancement of sleep slow oscillations and concomitant memory improvement in older adults," Front. Hum. Neurosci., vol. 11, No. March, pp. 1-14, 2017.

C. Diep, et al, "Enhancing Slow Wave Activity via an Automated Phase Locked Acoustic Stimulation," in Sleep 2017, 31st Annual Meeting of the Associated Professional Sleep Societies (APSS), 2017, p. A301.

Y. D. Van Der Werf, et al, "Reduction of nocturnal slow-wave activity affects daytime vigilance lapses and memory encoding but not reaction time or implicit learning," in Progress in Brain Research, vol. 193, 2011, pp. 245-255.

D.-J. Dijk, et al, "Selective SWS/SWA deprivation is associated with increased daytime sleep propensity in young, middle-aged and older men and women," in 18th Congress of the European-Sleep-Research-Society, 2006, pp. Sep. 12, 2006-Sep. 16, 2006.

* cited by examiner

SYSTEM AND METHOD FOR DELIVERING SENSORY STIMULATION TO A USER TO ENHANCE A COGNITIVE DOMAIN IN THE USER

BACKGROUND

1. Field

The present disclosure pertains to a system and method for delivering sensory stimulation to a user to enhance a cognitive domain in the user.

2. Description of the Related Art

Systems for monitoring sleep are known. The restorative value of sleep can be increased by delivering appropriately timed auditory stimulation during deep sleep to enhance sleep slow waves. Typical systems often adjust the auditory stimulation based on the brain activity of a user. Typical systems do not adjust therapy levels and/or patterns of stimulation provided to a user during sleep sessions based on targeted cognitive domains in the user.

SUMMARY

Accordingly, one or more aspects of the present disclosure relate to a system configured to deliver sensory stimulation during sleep to a user to enhance a target cognitive domain in the user. The system comprises one or more sensory stimulators, one or more sensors, one or more hardware processors, and/or other components. The one or more sensory stimulators are configured to provide sensory stimulation to the user during the sleep session. The one or more sensors are configured to generate output signals conveying information related to brain activity of the user during the sleep session. The one or more hardware processors are coupled to the one or more sensory stimulators and the one or more sensors. The one or more hardware processors are configured by machine readable instructions. The one or more hardware processors are configured to obtain an indication of the target cognitive domain for enhancement in the user. The target cognitive domain is associated with a stimulation strategy and a quantification method for quantifying an effect of sensory stimulation delivered according to the stimulation strategy. The stimulation strategy indicates a pattern (e.g., pitch for auditory stimulation, vibration frequency for somatosensory stimulation, etc.), a timing, and/or an intensity of the sensory stimulation provided to the user. The one or more hardware processors are configured to determine one or more brain activity parameters of the user during the sleep session based on the output signals and determine whether the one or more brain activity parameters indicate depth of the user's sleep. Responsive to the one or more brain activity parameters indicating the user is in sufficiently deep sleep, the one or more hardware processors are configured to cause the one or more sensory stimulators to provide the sensory stimulation to the user according to the stimulation strategy associated with the target cognitive domain, and determine the effect of the sensory stimulation provided to the user using the quantification method associated with the stimulation strategy and the target cognitive domain.

Another aspect of the present disclosure relates to a method for delivering sensory stimulation to a user to enhance a target cognitive domain in the user during a sleep session with a sensory stimulation system. The system comprises one or more sensory stimulators, one or more sensors, one or more hardware processors, and/or other components. The one or more hardware processors are configured by machine readable instructions. The method comprises providing, with the one or more sensory stimulators, sensory stimulation to the user during the sleep session. The method comprises generating, with the one or more sensors, output signals conveying information related to brain activity of the user during the sleep session. The method comprises obtaining, with the one or more hardware processors, an indication of the target cognitive domain for enhancement in the user. The target cognitive domain is associated with a stimulation strategy and a quantification method for quantifying an effect of sensory stimulation delivered according to the stimulation strategy. The stimulation strategy indicates a pattern (e.g., pitch for auditory stimulation, vibration frequency for somatosensory stimulation, etc.), a timing, and/or an intensity of the sensory stimulation provided to the user. The method comprises determining, with the one or more hardware processors, one or more brain activity parameters of the user during the sleep session based on the output signals. The method comprises determining, with the one or more hardware processors, whether the one or more brain activity parameters indicate the user is in sufficiently deep sleep. The method comprises, responsive to the one or more brain activity parameters indicating the user is in deep sleep, causing, with the one or more hardware processors, the one or more sensory stimulators to provide the sensory stimulation to the user according to the stimulation strategy associated with the target cognitive domain, and determining, with the one or more hardware processors, the effect of the sensory stimulation provided to the user using the quantification method associated with the stimulation strategy and the target cognitive domain.

Yet another aspect of the present disclosure relates to a system for delivering sensory stimulation during a sleep session to a user to enhance a target cognitive domain in the user. The system comprises means for providing sensory stimulation to the user during the sleep session. The system comprises means for generating output signals conveying information related to brain activity of the user during the sleep session. The system comprises means for obtaining an indication of the target cognitive domain for enhancement in the user. The target cognitive domain is associated with a stimulation strategy and a quantification method for quantifying an effect of sensory stimulation delivered according to the stimulation strategy. The stimulation strategy indicates a pattern (e.g., pitch for auditory stimulation, vibration frequency for somatosensory stimulation, etc.), a timing, and/or an intensity of the sensory stimulation provided to the user. The system comprises means for determining one or more brain activity parameters of the user during the sleep session based on the output signals. The system comprises means for determining whether the one or more brain activity parameters indicate the user is in sufficiently deep sleep. The system comprises means for, responsive to the one or more brain activity parameters indicating the user is in deep sleep, causing the one or more sensory stimulators to provide the sensory stimulation to the user according to the stimulation strategy associated with the target cognitive domain, and determining the effect of the sensory stimulation provided to the user using the quantification method associated with the stimulation strategy and the target cognitive domain.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
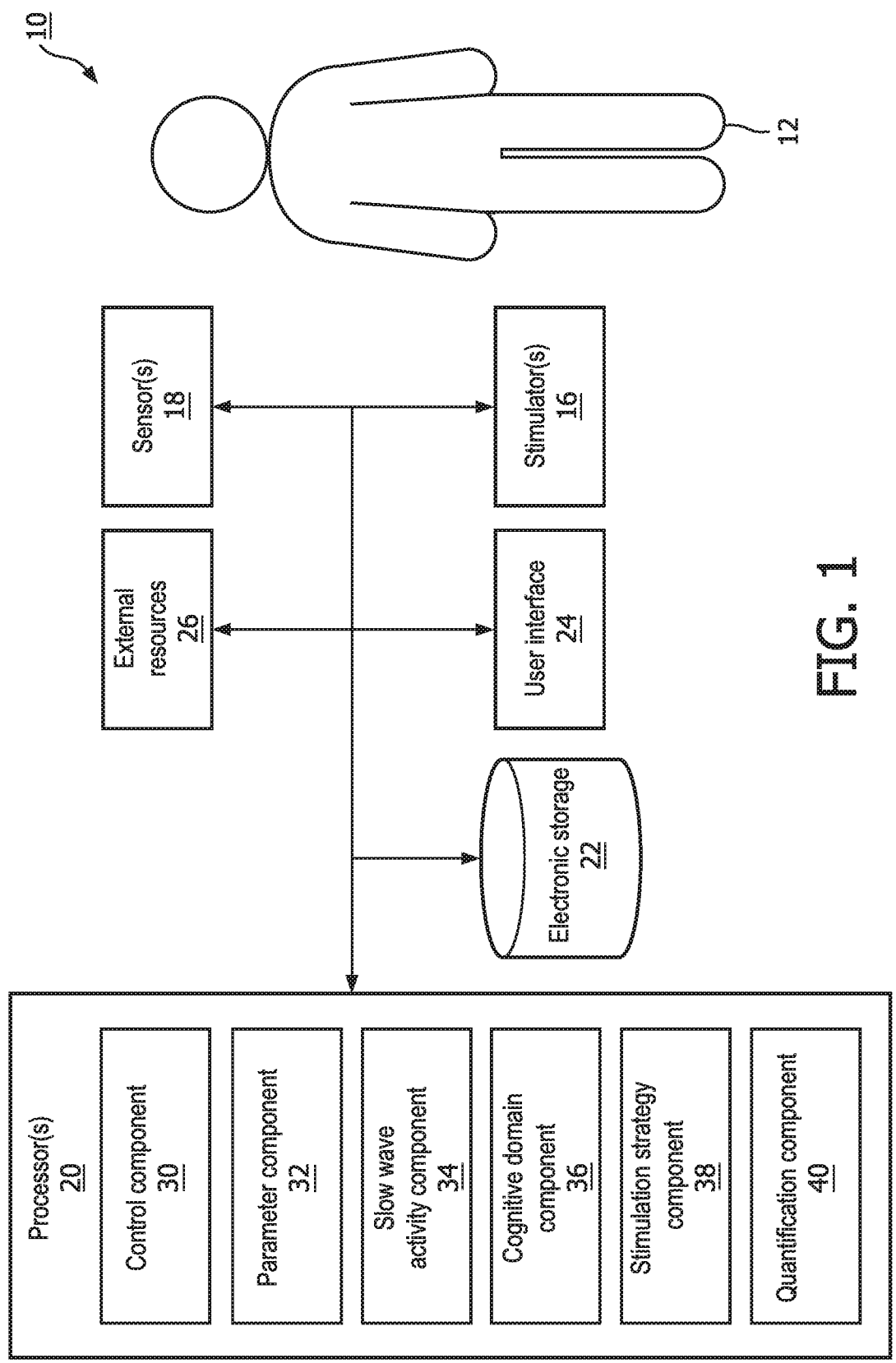
FIG. 1 is a schematic illustration of a system configured to deliver sensory stimulation to a user to enhance a cognitive domain in the user.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic illustration of a system 10 configured to deliver sensory stimulation to a user 12 to restore and/or enhance a cognitive domain in user 12 and/or for other purposes. In some embodiments, system 10 includes one or more of a stimulator 16, a sensor 18, a processor 20, electronic storage 22, a user interface 24, external resources 26, and/or other components. System 10 is configured such that sensory stimulation such as auditory and/or other stimulation delivered during sleep enhances slow waves in user 12, which brings cognitive benefits and enhancement of sleep restoration. As described herein, system 10 is configured to detect deep sleep in real-time and/or near real-time, and deliver sensory (e.g., auditory) stimulation to enhance sleep slow waves without causing arousals. System 10 is configured to apply different stimulation strategies (e.g., continuous stimulation, block stimulation, etc.) depending on which cognitive domain (e.g., memory, vigilance, verbal fluency, sleepiness, memory encoding, learning efficiency, etc.) is targeted for restoration and/or enhancement. In some embodiments, system 10 is configured to adjust parameters of the stimulation to cause user 12 to reach a cognitive performance goal.

Figure 2A:
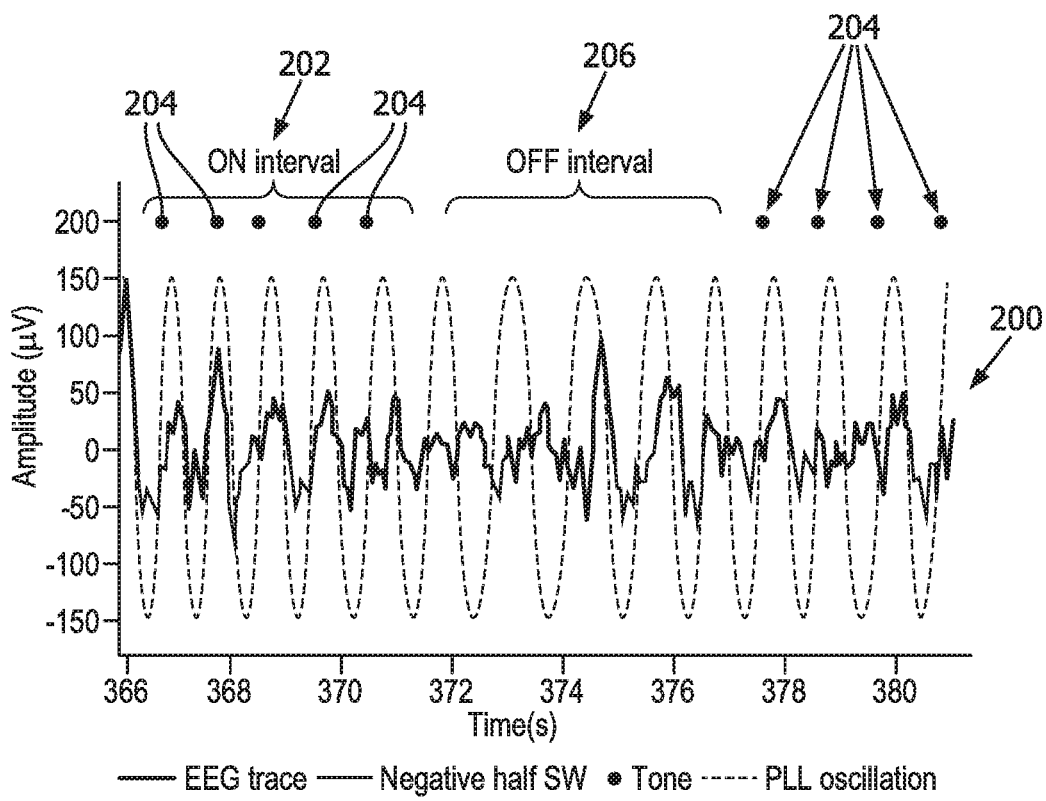
FIGS. 2A-2D illustrate increased slow wave activity produced by sensory stimulation from the system and the effect of the increased slow wave activity on the restoration and/or enhancement of various cognitive domains in users.
Figure 2B:
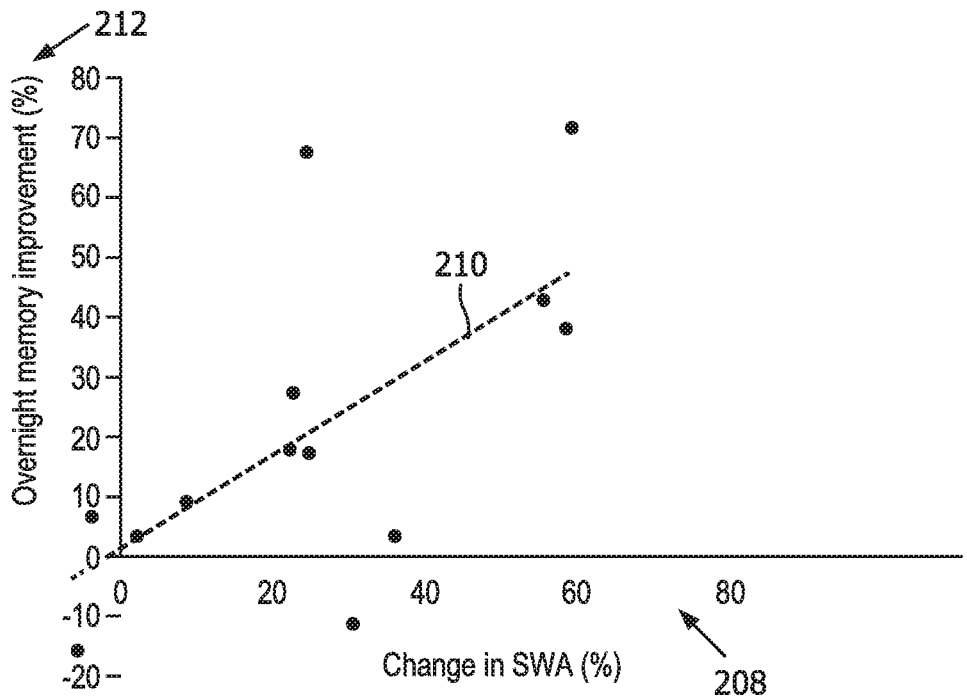
Figure 2C:
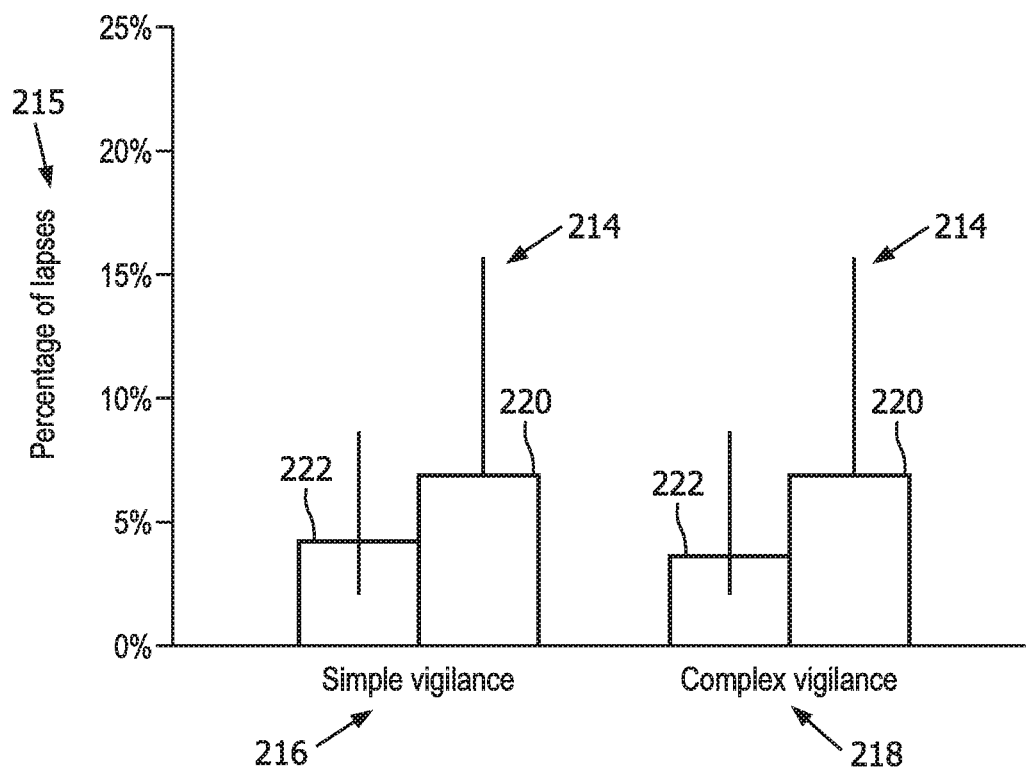
Figure 2D:
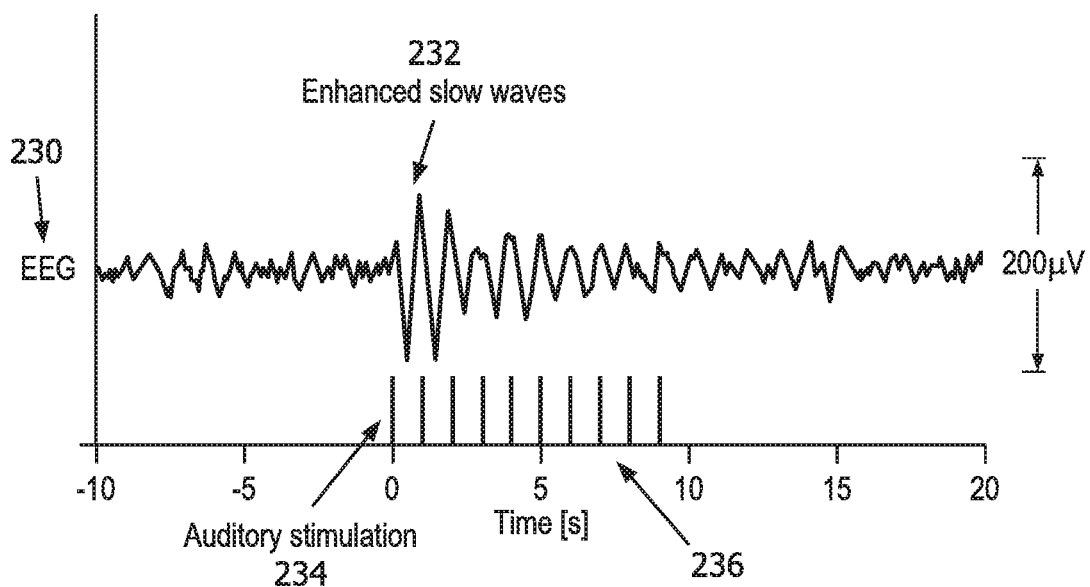

By way of a non-limiting example, FIGS. 2A-2D illustrate increased slow wave activity produced by sensory (e.g., auditory) stimulation from system 10 (FIG. 1) and the effect of the increased slow wave activity on the restoration and/or enhancement of various cognitive domains (memory improvement and vigilance in this example) in users (e.g., user 12 shown in FIG. 1). As shown in FIG. 2A, in some embodiments, system 10 (FIG. 1) is configured such that change in slow wave activity 200 is determined by comparing the slow wave activity in "ON" periods 202 where a predetermined number (e.g., 5 in this example) tones (also just for this example) 204 are applied, and slow wave activity 200 in subsequent and approximately equally long "OFF" periods 206 without stimulation. As shown in FIG. 2B, changes (e.g., increases) in slow wave activity 208 positively correlate 210 with memory enhancement 212. As shown in FIG. 2C, reductions in slow wave activity 214 during sleep (where the dark colored bars 220 for each type of vigilance task are representative of reduced slow wave activity compared to the light colored bars 222) correlate with reductions in vigilance as measured by a percentage of lapses 215 in a simple 216 and a complex 218 vigilance task. As shown in FIG. 2C, more lapses occur (bars 220 are taller than bars 222) when there was less slow wave activity during sleep. Changes in slow wave activity also correlate with the restoration and/or enhancement of other cognitive domains in addition to memory consolidation and vigilance mentioned above such as verbal fluency, sleepiness, memory encoding, learning efficiency, and/or other cognitive domains (not shown in FIG. 2C). Finally, FIG. 2D illustrates an electroencephalogram (EEG) signal 230 showing enhanced slow waves 232 that correspond to auditory (for example) stimulation 234 (e.g., where tones delivered to a user are indicated by vertical lines 236).

Returning to FIG. 1, sensory stimulator 16 is configured to provide sensory stimulation to user 12. Sensory stimulator 16 is configured to provide auditory, visual, somatosensory, electric, magnetic, and/or sensory stimulation to user 12 prior to a sleep session, during a sleep session, and/or at other times. In some embodiments, a sleep session may comprise any period of time when user 12 is sleeping and/or attempting to sleep. Sleep sessions may include nights of sleep, naps, and/or other sleeps sessions. For example, sensory stimulator 16 may be configured to provide stimuli to user 12 during a sleep session to facilitate a transition to a deeper stage of sleep, a lighter stage of sleep, maintain sleep in a specific stage, enhance a target cognitive domain (e.g., as described herein), and/or for other purposes. In some embodiments, sensory stimulator 16 may be configured such that facilitating a transition between deeper sleep stages and lighter sleep stages includes decreasing sleep slow waves in user 12, and facilitating a transition between lighter sleep stages and deeper sleep stages includes increasing sleep slow waves.

Sensory stimulator 16 is configured to facilitate transitions between sleep stages, maintain sleep in a specific stage, and/or enhance a target cognitive domain through non-invasive brain stimulation and/or other methods. Sensory stimulator 16 may be configured to facilitate transitions between sleep stages, maintain sleep in a specific stage, and/or enhance a target cognitive domain through non-invasive brain stimulation using auditory, electric, magnetic, visual, somatosensory, and/or other sensory stimuli. The auditory, electric, magnetic, visual, somatosensory, and/or other sensory stimulation may include auditory stimulation, visual stimulation, somatosensory stimulation, electrical stimulation, magnetic stimulation, a combination of different types of stimulation, and/or other stimulation. The auditory, electric, magnetic, visual, somatosensory, and/or other sensory stimuli include odors, sounds, visual stimulation, touches, tastes, somatosensory stimulation, haptic, electrical, magnetic, and/or other stimuli. For example, acoustic tones may be provided to user 12 to enhance a target cognitive domain in user 12. Examples of sensory stimulator 16 may include one or more of a sound generator, a speaker, a music player, a tone generator, one or more electrodes on the scalp of user 12, a vibrator (such as a piezoelectric member, for example) to deliver vibratory stimulation, a coil generating a magnetic field to directly stimulate the brain's cortex, one or more light generators or lamps, a fragrance dispenser, and/or other devices. In some embodiments, sensory stimulator 16 is configured to adjust the intensity, timing, and/or other parameters of the stimulation provided to user 12 (e.g., as described herein).

Sensor 18 is configured to generate output signals conveying information related to brain activity and/or other activity in user 12. In some embodiments, sensor 18 is configured to generate output signals conveying information related to slow wave activity (SWA) in user 12. In some embodiments, the information related to brain activity and/or other activity in user 12 is the information related to SWA. In some embodiments, sensor 18 is configured to generate output signals conveying information related to stimulation provided to user 12 during sleep sessions.

In some embodiments, the SWA of user 12 may be used to detect a sleep stage of user 12. The sleep stage of user 12 may be associated with rapid eye movement (REM) sleep, non-rapid eye movement (NREM) sleep, and/or other sleep. The sleep stage of user 12 may be one or more of NREM stage N1, stage N2, or stage N3, REM sleep, and/or other sleep stages. In some embodiments, the sleep stage of user 12 may be one or more of stage S1, S2, S3, or S4. In some embodiments, NREM stage 2 and/or 3 (and/or S3 and/or S4) may be slow wave (e.g., deep) sleep. Sensor 18 may comprise one or more sensors that measure such parameters directly. For example, sensor 18 may include electroencephalogram (EEG) electrodes configured to detect electrical activity along the scalp of user 12 resulting from current flows within the brain of user 12. Sensor 18 may comprise one or more sensors that generate output signals conveying information related to SWA of user 12 indirectly. For example, one or more sensors 18 may comprise a heart rate sensor that generates an output based on a heart rate of user 12 (e.g., sensor 18 may be a heart rate sensor than can be located on the chest of user 12, and/or be configured as a bracelet on a wrist of user 12, and/or be located on another limb of user 12), movement of user 12 (e.g., sensor 18 may comprise an accelerometer that can be carried on a wearable, such as a bracelet around the wrist and/or ankle of user 12 such that sleep may be analyzed using actigraphy signals), respiration of user 12, and/or other characteristics of user 12.

In some embodiments, sensor 18 may comprise one or more of the EEG electrodes, an electrooculogram (EOG) electrode, an actigraphy sensor, an electrocardiogram (EKG) electrode, a respiration sensor, a pressure sensor, a vital signs camera, a photoplethysmogram (PPG) sensor, a functional near infra-red sensor (fNIR), a temperature sensor, a microphone and/or other sensors configured to generate output signals related to (e.g., the quantity, frequency, intensity, and/or other characteristics of) the stimulation provided to user 12, and/or other sensors. Although sensor 18 is illustrated at a single location near user 12, this is not intended to be limiting. Sensor 18 may include sensors disposed in a plurality of locations, such as for example, within (or in communication with) sensory stimulator 16, coupled (in a removable manner) with clothing of user 12, worn by user 12 (e.g., as a headband, wristband, etc.), positioned to point at user 12 while user 12 sleeps (e.g., a camera that conveys output signals related to movement of user 12), coupled with a bed and/or other furniture where user 12 is sleeping, and/or in other locations.

Figure 3:
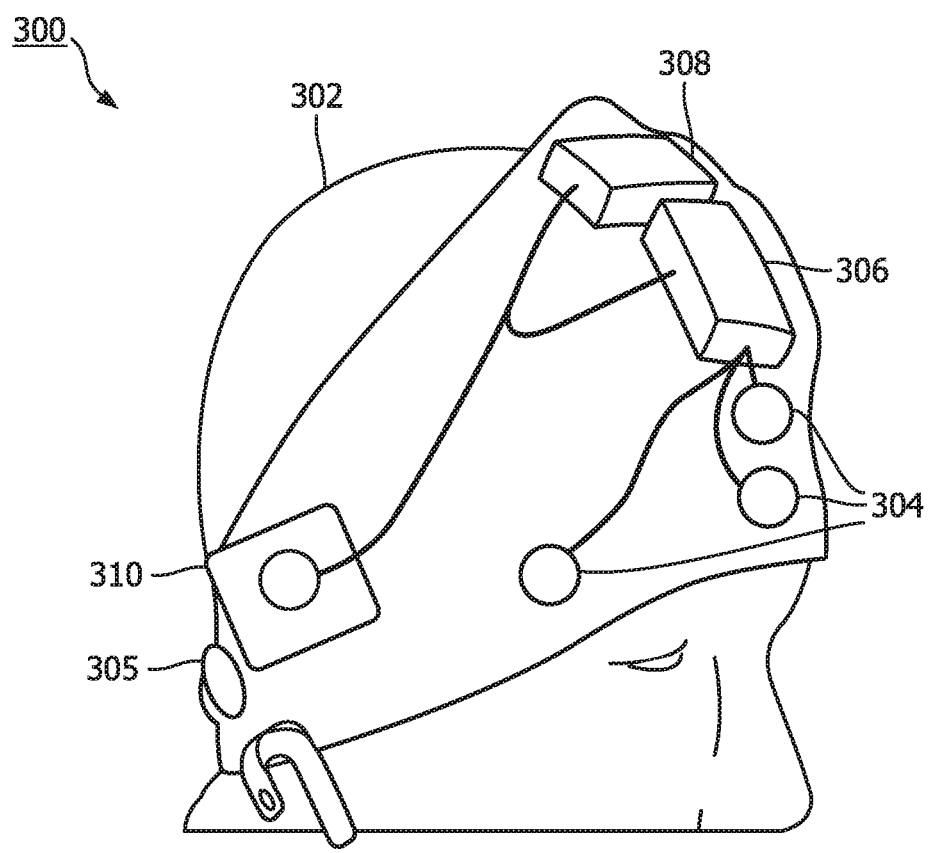
FIG. 3 illustrates a headset worn by the user including sensing electrodes, a reference electrode, one or more devices associated with an electroencephalogram, a wired and/or wireless audio device, and means to delivery auditory stimulation (e.g., one or more audio speakers and/or other devices).

In FIG. 1, sensory stimulator 16, sensor 18, processor 20, electronic storage 22, and user interface 24 are shown as separate entities. This is not intended to be limiting. Some and/or all of the components of system 10 and/or other components may be grouped into one or more singular devices. For example, FIG. 3 illustrates a headset 300 worn by a user 302. Headset 300 includes sensing electrodes 304, a reference electrode 305, one or more devices associated with an EEG 306, means to deliver auditory stimulation (e.g., a wired and/or wireless audio device and/or other devices) 308, and one or more audio speakers 310. Audio speakers 310 may be located in and/or near the ears of user 302 and/or in other locations. The reference electrode 305 may be located behind the ear of user 302, and/or in other locations. In the example shown in FIG. 3, sensing electrodes 304 may be configured to generate output signals conveying information related to brain activity of user 302, and/or other information. The output signals may be transmitted to a processor (e.g., processor 20 shown in FIG. 1), a computing device (e.g., a bedside laptop) which may or may not include the processor, and/or other devices wirelessly and/or via wires. Acoustic stimulation may be delivered to user 302 via wireless audio device 308 and/or speakers 310. Sensing electrodes 304, reference electrode 305, and devices 306 may be represented, for example, by sensor 18 in FIG. 1. Wireless audio device 308 and speakers 310 may be represented, for example, by sensory stimulator 16 shown in FIG. 1. In this example, a computing device (not shown in FIG. 3) may include processor 20, electronic storage 22, user interface 24, and/or other components of system 10 shown in FIG. 1.

Returning to FIG. 1, processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device (e.g., sensory stimulator 16, user interface 24, etc.), or processor 20 may represent processing functionality of a plurality of devices operating in coordination. In some embodiments, processor 20 may be and/or be included in a computing device such as a desktop computer, a laptop computer, a smartphone, a tablet computer, a server, and/or other computing devices. Such computing devices may run one or more electronic applications having graphical user interfaces configured to facilitate user interaction with system 10.

As shown in FIG. 1, processor 20 is configured to execute one or more computer program components. The computer program components may comprise software programs and/or algorithms coded and/or otherwise embedded in processor 20, for example. The one or more computer program components may comprise one or more of a control component 30, a parameter component 32, a slow wave activity component 34, a cognitive domain component 36, a stimulation strategy component 38, a quantification component 40, and/or other components. Processor 20 may be configured to execute components 30, 32, 34, 36, 38, and/or 40 by software; hardware; firmware; some combination of software, hardware, and/or firmware; and/or other mechanisms for configuring processing capabilities on processor 20.

It should be appreciated that although components 30, 32, 34, 36, 38, and 40 are illustrated in FIG. 1 as being co-located within a single processing unit, in embodiments in which processor 20 comprises multiple processing units, one or more of components 30, 32, 34, 36, 38, and/or 40 may be located remotely from the other components. The description of the functionality provided by the different components 30, 32, 34, 36, 38, and/or 40 described below is for illustrative purposes, and is not intended to be limiting, as any of components 30, 32, 34, 36, 38, and/or 40 may provide more or less functionality than is described. For example, one or more of components 30, 32, 34, 36, 38, and/or 40 may be eliminated, and some or all of its functionality may be provided by other components 30, 32, 34, 36, 38, and/or 40. As another example, processor 20 may be configured to execute one or more additional components that may perform some or all of the functionality attributed below to one of components 30, 32, 34, 36, 38, and/or 40.

Control component 30 is configured to control one or more stimulators 16 to provide stimulation to user 12 during sleep sessions and/or at other times. In some embodiments, stimulators 16 are controlled to provide stimulation according to a predetermined therapy regime. Sleep slow waves can be enhanced through (e.g. peripheral auditory, magnetic, electrical, and/or other) stimulation delivered in NREM sleep. Control component 30 (and/or parameter component 32 described below) monitors the brain activity of user 12 based on the output signals of sensors 18 (e.g., based on an EEG) and/or other information during sleep sessions and controls the delivery of stimulation (e.g., auditory and/or other stimulation) by stimulator 16 to control SWA in user 12. In some embodiments, control component 30 (and/or or more of the other processor components described below) performs one or more operations similar to and/or the same as the operations described in U.S. patent application Ser. No. 14/784,782 (entitled "System and Method for Sleep Session Management Based on Slow Wave Sleep Activity in a Subject"), Ser. No. 14/783,114 (entitled "System and Method for Enhancing Sleep Slow Wave Activity Based on Cardiac Activity"), Ser. No. 14/784,746 (entitled "Adjustment of Sensory Stimulation Intensity to Enhance Sleep Slow Wave Activity"), Ser. No. 15/101,008 (entitled "System and Method for Determining Sleep Stage Based on Sleep Cycle"), and/or Ser. No. 15/100,435 (entitled "System and Method for Facilitating Sleep Stage Transitions"), which are all individually incorporated by reference in their entireties.

Parameter component 32 is configured to determine one or more brain activity parameters for user 12. The one or more brain activity parameters are determined based on the output signals and/or other information. In some embodiments, determining one or more brain activity parameters may include generating and/or monitoring an EEG during a sleep session of user 12. The EEG may be displayed, for example, by user interface 24. In some embodiments, parameter component 32 is configured such that the one or more brain activity parameters are and/or are related to a frequency, amplitude, phase, presence of specific sleep patterns such as spindles, K-complexes, or sleep slow waves, alpha waves, and/or other characteristics of an EEG signal. In some embodiments, the one or more brain activity parameters are determined based on the frequency, amplitude, and/or other characteristics of the EEG signal. In some embodiments, the determined brain activity parameters and/or or the characteristics of the EEG may be and/or indicate sleep stages that correspond to the REM and/or NREM sleep stages described above.

For example, typical EEG characteristics during NREM sleep include a transition from alpha waves (e.g., about 8-12 Hz) to theta waves (e.g., about 4-7 Hz) for sleep stage N1; presence of sleep spindles (e.g., about 11 to 16 Hz) and/or K-complexes (e.g., similar to sleep slow waves) for sleep stage N2; presence of delta waves (e.g., about 0.5 to 4 Hz), also known as sleep slow waves, with peak-to-peak amplitudes greater than about 75 uV for sleep stage N3; presence of light sleep and/or arousals, and/or other characteristics. In some embodiments, light sleep may be characterized by the fact that the alpha activity (e.g., EEG power in the 8-12 Hz band) is no longer present and slow waves are not present. In some embodiments, SWA is a continuous value (e.g., EEG power in the 0.4 to 4 Hz band), which is positive. System 10 may be configured to detect its absence by comparing the SWA in user 12 to a threshold. In some embodiments, an absence of slow waves is indicative of light sleep. In addition, spindle activity (EEG power in the 11 to 16 Hz band) may be high. Deep sleep may be characterized by the fact that delta activity (e.g., EEG power in the 0.5 to 4 Hz band) is dominant. In some embodiments, EEG power in the delta band and SWA are the same when considering sleep EEG. In some embodiments, parameter component 32 is configured to determine a change in an EEG delta power level caused by the stimulation, a quantity of micro arousals in user 12, other EEG power levels, and/or other parameters.

In some embodiments, parameter component 32 is configured to determine the one or more brain activity parameters and/or other parameters at predetermined times (e.g., intervals), substantially continuously, and/or at other times. In some embodiments, brain activity parameters may be determined based on the EEG signals, electrocardiogram (ECG) signals, actigraphy signals, body temperature signals, galvanic skin response (GSR) signals, and/or other information related to the brain, the central and/or peripheral nervous systems of user 12, and/or other biological systems of user 12.

By way of a non-limiting example, in some embodiments, sensor 18 comprises one or more electroencephalogram (EEG) electrodes (e.g., as described herein). Based on information in output signals from sensors 18, control component 30 and/or parameter component 32 are configured to detect sleep micro-arousals by determining the EEG power in the alpha (8-12 Hz) and beta (15-30 Hz) frequency bands, and comparing the EEG power to pre-established thresholds. Control component 30 and/or parameter component 32 are configured such that the presence of an arousal delays the onset of subsequent (e.g., auditory) stimulation. Control component 30 and/or parameter component 32 are configured such that ongoing stimulation stops responsive to an arousal being detected. In some embodiments, control component 30 and/or parameter component 32 are configured such that the stimulation provided to user 12 is auditory stimulation comprising 50-millisecond long tones and/or tones of other lengths separated from each other by fixed 1-second long inter-tone intervals and/or other inter-tone intervals. In some embodiments, auditory stimulation is timed to coincide with a specific phase of a detected slow wave. In some embodiments, control component 30 and/or parameter component 32 are configured such that the volume, length, timing, and/or other parameters of individual tones (and/or the intensity and/or timing of other types of stimulation) is modulated by sleep stage, sleep depth (e.g., ratio SWA/power in the beta (15 to 30 Hz)), target cognitive domain, and/or other information. In some embodiments, the tones and/or other sensory stimulation are modulated such that louder, longer, and/or more frequent tones (more intense stimulation) are delivered during deeper sleep and softer, shorter, and/or less frequent tones (less intense stimulation) are delivered during shallower sleep. This example is not intended to be limiting.

Slow wave activity component 34 is configured to determine whether user 12 is experiencing sufficiently deep sleep (e.g., stage N2 and/or N3) for sensory stimulation to begin and/or continue. In some embodiments, sufficiently deep sleep is sleep where detected NREM sleep is present and sleep depth in user 12 is higher than a pre-established threshold, for example. In some embodiments, this threshold may be determined based on information from previous sleep sessions of user 12, information from electronic storage 22, external resources 26, and/or other sources of information, information entered and/or selected via user interface 24, and/or determined based on other information.

SWA is the EEG power in the 0.5 to 4 Hz band (e.g., as described above). In some embodiments, slow wave activity component 34 is configured to determine a level of slow wave activity in user 12, detect slow wave events, detect N1, N2, and/or N3 sleep, and/or determine other information. Slow wave activity component 34 is configured to determine whether user 12 is experiencing sufficiently deep sleep based on information from sensor 18, information from control component 30, information from parameter component 32, and/or other information. In some embodiments, responsive to no arousal being detected (e.g., as described above), slow wave activity component 34 is configured to determine a type of (e.g., NREM) sleep by, for example, determining EEG power in the 0.5 to 4 Hz frequency band, which indicates SWA, and quantifying a density of slow waves in the EEG signal. Control component 30 and/or parameter component 32 are configured to provide stimulation responsive a determination by slow wave activity component 34 that user 12 is experiencing NREM and/or slow wave sleep.

In some embodiments, the determination by slow wave activity component 34 that user 12 is experiencing slow wave sleep comprises a first determination that user 12 is experiencing NREM sleep and a second determination that user 12 is experiencing slow wave sleep. In embodiments where continuous stimulation is delivered to user 12 (e.g., as described below), control component 30 and/or parameter component 32 may be configured to begin providing stimulation to user 12 after the determination that user 12 is experiencing NREM sleep. In embodiments where block stimulation is delivered to user 12 (e.g., as described below), control component 30 and/or parameter component 32 may be configured to begin providing stimulation to user 12 only after the determination that user 12 is experiencing slow wave sleep. In some embodiments, the determination by slow wave activity component 34 that user 12 is experiencing slow wave sleep comprises a determination that the duration of detected sleep of a specific type (e.g., NREM) breaches a duration threshold (e.g., at least 1.5 minutes—this example is not intended to be limiting), and a sleep depth (e.g., determined based on a ratio between delta and beta powers in the EEG signal) breaching a sleep depth threshold. In some embodiments, slow wave activity component 34 is configured to determine whether user 12 is experiencing slow wave sleep in an ongoing manner, at predetermined intervals, and/or at other times with or without regard for whether arousals have been detected. In some embodiments, the timing of these determinations (e.g., in an ongoing manner, at predetermined intervals, etc.) is determined at manufacture of system 10, based on information from sensor 18, based on information from control component 30 and/or parameter component 32, based on information entered and/or selected via user interface 24, based on information from electronic storage 22, based on information from external resources 26, and/or based on other information.

Cognitive domain component 36 is configured to obtain an indication of a target cognitive domain. In some embodiments, the target cognitive domain comprises one or more of memory consolidation, vigilance, verbal fluency, sleepiness, memory encoding, learning efficiency, and/or other cognitive domains. In general, cognitive domains include domains related to attention (or vigilance), memory, and executive function, all of which can be addressed by this device. In some embodiments, memory consolidation may refer to the ability of user 12 and/or other users to remember things seen, heard, read, experienced, etc. Vigilance may refer to an ability of user 12 and/or other users to maintain focus on a task and/or other activities without being substantially distracted or without substantial lapses in focus. Verbal fluency may refer to an ability of user 12 and/or other users to access their mental lexicon and verbally communicate in a clear and effective manner. The sleepiness cognitive domain may refer to the alertness and/or drowsiness of user 12 and/or other users while not sleeping. It should be noted that the examples of cognitive domains and their corresponding descriptions are not intended to be limiting. Any number of cognitive domains are contemplated for restoration and/or enhancement by system 10.

In some embodiments, cognitive domain component 36 is configured such that obtaining an indication of a target cognitive domain includes facilitating entry and/or selection of the indication of the target cognitive domain via user interface 24 and/or other interfaces. In some embodiments, cognitive domain component 36 is configured such that obtaining an indication of a target cognitive domain includes facilitating entry and/or selection of the indication of the target cognitive domain via a software application by user 12, one or more caregivers of user 12, and/or other users. A caregiver may include a doctor, a nurse, and/or other medical staff caring for user 12; friends and/or family members of user 12; researchers; and/or other caregivers. The software application may be run by system 10 (e.g., and displayed via user interface 24), a computing system (e.g., a smartphone, a laptop computer, a desktop computer, a tablet computer, etc.) associated with user 12 and/or a caregiver, and/or may be run on other computing systems. The software application may be accessed by the caregivers, user 12, and/or other users via a graphical user interface running on these and/or other computing devices. In some embodiments, the indication of a target cognitive domain is obtained from one or more external databases included in external resources 26 (e.g., a medical records database associated with a health care provider), electronic storage 22 included in system 10, one or more sensors 18, and/or other sources of information. In some embodiments, the indication of a target cognitive domain may be obtained via text, email, phone, call and/or other communication methods. In some embodiments, the target cognitive domain may be programmed at manufacture of system and/or determined by other methods.

Stimulation strategy component 38 is configured to determine a stimulation strategy for controlling stimulator 16 to deliver the sensory stimulation to user 12. In some embodiments, the target cognitive domain obtained by cognitive domain component 36 is associated with a stimulation strategy and/or other information. In some embodiments, stimulation strategy component 38 is configured to determine the stimulation strategy for controlling stimulator 16 based on these associations and/or other information. In some embodiments, these associations are stored in electronic storage 22, stored in external resources 26, and/or stored in other locations. In such embodiments, stimulation strategy component 38 is configured to electronically access the stored associations and/or access the stored associations in other ways. Examples of these associations are shown in Table I.

TABLE I

Cognitive Domain Associated With Stimulation Strategy and Quantification Method

| Cognitive Domain | Stimulation Strategy | Quantification Method |
| --- | --- | --- |
| Memory consolidation | Block stimulation | SWA change between ON blocks and flanking OFF blocks |
| Vigilance | Continuous stimulation | Average SWA |
| Verbal fluency | Continuous stimulation | Total SWA across N3 sleep |
| Sleepiness | Continuous stimulation | Average SWA |

The stimulation strategy may indicate a pattern, a timing, and/or an intensity of the sensory stimulation provided to the user. In some embodiments, as shown in Table I, the memory consolidation target cognitive domain is associated with a block stimulation strategy. In some embodiments, a block stimulation strategy comprises repeating periods of time where stimulation (e.g., audible tones have a specified volume, length, and inter tone interval) is delivered to user 12 followed by periods of time where no stimulation is delivered to user 12. In some embodiments, blocks may be up to about 15 seconds long and/or have other lengths. In some embodiments, also as shown in Table I, the vigilance, verbal fluency, and sleepiness target cognitive domains are associated with continuous stimulation strategies. In some embodiments, a continuous stimulation strategy comprises providing sensory stimulation to user 12 regularly throughout (at least during slow wave sleep as described herein) a sleep session. Stimulation strategy component 38 is configured to cause stimulator 16 to deliver the sensory stimulation according to the stimulation strategy associated with the target cognitive domain (as shown in Table I).

By way of a non-limiting example, for the vigilance, verbal fluency, and sleepiness target cognitive domains, which are associated with continuous stimulation, stimulation strategy component 38 is configured to cause sensory stimulator 16 to deliver stimulation whenever NREM sleep is detected, sleep depth (quantified by the ratio between EEG delta power to EEG beta power) is sufficient to breach a sleep depth threshold associated with deep and/or slow wave sleep, and few to no sleep micro-arousals have been detected. For the memory consolidation target cognitive domain, which is associated with block stimulation, (e.g., N=15) tones in an ON-block may be alternated with periods of no-stimulation (e.g., OFF blocks of approximately the same length of time). The block based SWA enhancement (or local SWA enhancement) is determined as the change of SWA during ON blocks compared to SWA during OFF blocks (as shown in Table I and described below).

In some embodiments, the stimulation delivered to user 12 with a block stimulation strategy and/or a continuous stimulation strategy may be adjusted as described herein within blocks, block to block, at other intervals, and/or continuously. In some embodiments, these adjustments may be based on information from one or more previous sleep sessions of user 12, information entered and/or selected via user interface 24 (e.g., indicating user specific stimulation parameters and/or other information), information from one or more electronic databases (e.g., electronic storage 22, external resources 26, etc.), and/or other information. In some embodiments, a quantity, intensity, duration, interval, and/or other parameters of individual stimuli may be adjusted. In some embodiments, these adjustments may personalize a stimulation strategy for user 12, for example. In some embodiments, stimulation strategy component 38 is configured to control and/or otherwise cause stimulator 16 to provide the sensory stimulation to user 12 according to the determined stimulation strategy (e.g., block, continuous, etc.) with the adjustments. As described above, stimulator 16 is caused to provide the sensory stimulation according to the stimulation strategy associated with the target cognitive domain responsive to the one or more brain activity parameters indicating the user is in deep sleep.

Quantification component 40 is configured to quantify the effect of the sensory stimulation delivered according to the stimulation strategy. In some embodiments, the target cognitive domain is associated with a quantification method for quantifying an effect of sensory stimulation delivered according to the stimulation strategy. Examples of these associations are shown in Table I. Quantification component 40 is configured to determine which quantification method to use to quantify the effect of the sensory stimulation based on these associations and/or other information. Quantification component 40 is configured such that the effect of the sensory stimulation provided to the user is determined using the quantification method associated with the stimulation strategy and the target cognitive domain. In some embodiments, these associations are stored in electronic storage 22, stored in external resources 26, and/or stored in other locations. In such embodiments, quantification component 40 is configured to electronically access the stored associations and/or access the stored associations in other ways.

In some embodiments, as shown in Table I, quantification component 40 is configured such that the memory consolidation target cognitive domain is associated with a quantification method comprising determining a SWA change in the user during "on" and "off" blocks of sensory stimulation during the sleep session. In some embodiments, determining a SWA change in user 12 during ON and OFF stimulation comprises determining a resulting amount of SWA in user 12 during and/or immediately following individual blocks. In some embodiments, a larger difference in SWA resulting from ON blocks compared to OFF blocks corresponds to increased memory consolidation in user 12.

In some embodiments, the verbal fluency target cognitive domain is associated with a quantification method comprising determining total SWA in the user during deep sleep in the sleep session. In some embodiments, quantification component 40 is configured such that determining total SWA comprises a summation and/or other accumulation of SWA in user 12 up to a given point during a sleep session and increases throughout the sleep session. In some embodiments, a higher total SWA amount corresponds to a greater increase in verbal fluency.

In some embodiments, the vigilance target cognitive domain is associated with a quantification method comprising determining average SWA in the user during the sleep session. In some embodiments, the sleepiness target cognitive domain is associated with a quantification method comprising determining the average SWA in the user during the sleep session. In some embodiments, quantification component 40 is configured such that analyzing average SWA in user 12 for a sleep session comprises determining individual amounts and/or levels of SWA in user 12 at various times during the sleep session and averaging the individual amounts and/or levels for the sleep session. In some embodiments, analyzing average SWA comprises comparing average SWA for a sleep session with stimulation and a sleep session without stimulation. In some embodiments, a higher average SWA corresponds to increased vigilance and/or less sleepiness in user 12.

In some embodiments, SWA may be compared between blocks where stimulation is present or absent or across substantially entire nights (sleep sessions) with and without stimulation. In some embodiments, SWA may be compared across all N3 or NREM for a night (sleep session) with and without stimulation. In some embodiments, the comparison of SWA between blocks may be referred to as local SWA comparison; the comparison of SWA across N3 for a night (sleep session) with and without stimulation may be referred to as global, across N3, and/or SWA comparison; and/or the comparison of SWA across NREM for a night with and without stimulation can be referred to as global, across NREM, and/or SWA comparison.

Figure 4A:
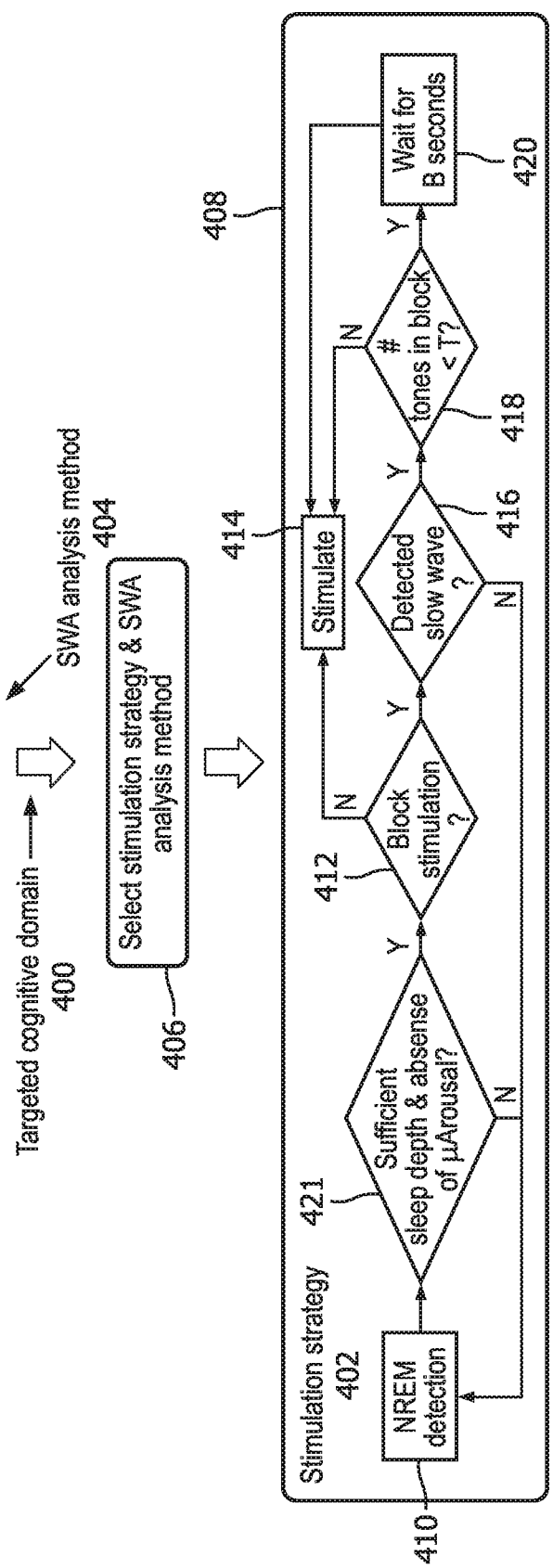
FIGS. 4A and 4B illustrate operations performed by a cognitive domain component, a stimulation strategy component, and a quantification component of the system.

By way of a non-limiting example, FIG. 4A illustrates operations performed by cognitive domain component 36 (FIG. 1), stimulation strategy component 38 (FIG. 1), quantification component 40 (FIG. 1), and/or other components of system 10 (FIG. 1). As shown in FIG. 4A, an indication 400 of a target cognitive domain is received (e.g., one of the examples listed in Table I which is reproduced in FIG. 4A). Based on indication 400 of the target cognitive domain, a stimulation strategy 402 and a SWA analysis (quantification) method 404 are determined 406. As shown in operational block 408 and described above, the system is configured to detect NREM sleep 410 and determine whether to begin providing sensory stimulation by determining 421 whether sleep depth and an absence of micro-arousals indicate deep and/or slow wave sleep, and determining 412 whether stimulation strategy 402 comprises block stimulation. Responsive to stimulation strategy 402 comprising continuous stimulation (not block stimulation), stimulation 414 commences. Otherwise, system 10 (FIG. 1) determines 416 whether a user (e.g., user 12 shown in FIG. 1) is experiencing sufficiently deep sleep, and whether 418 a number of tones in a given block is less than a threshold level. If so, stimulation commences 414. If not, the system waits 420 a predetermined "B" amount of time and repeats the detection process. In some embodiments, determining whether the block has less than a threshold number of tones (e.g., step 418 in FIG. 4A) indicates that stimulation is delivered while the number of tones is lower than a target number of tones. From the moment the targeted number of tones has been delivered, system 10 is configured to wait for B seconds (e.g., the duration of the OFF blocks as shown in FIG. 4A).

Figure 4B:
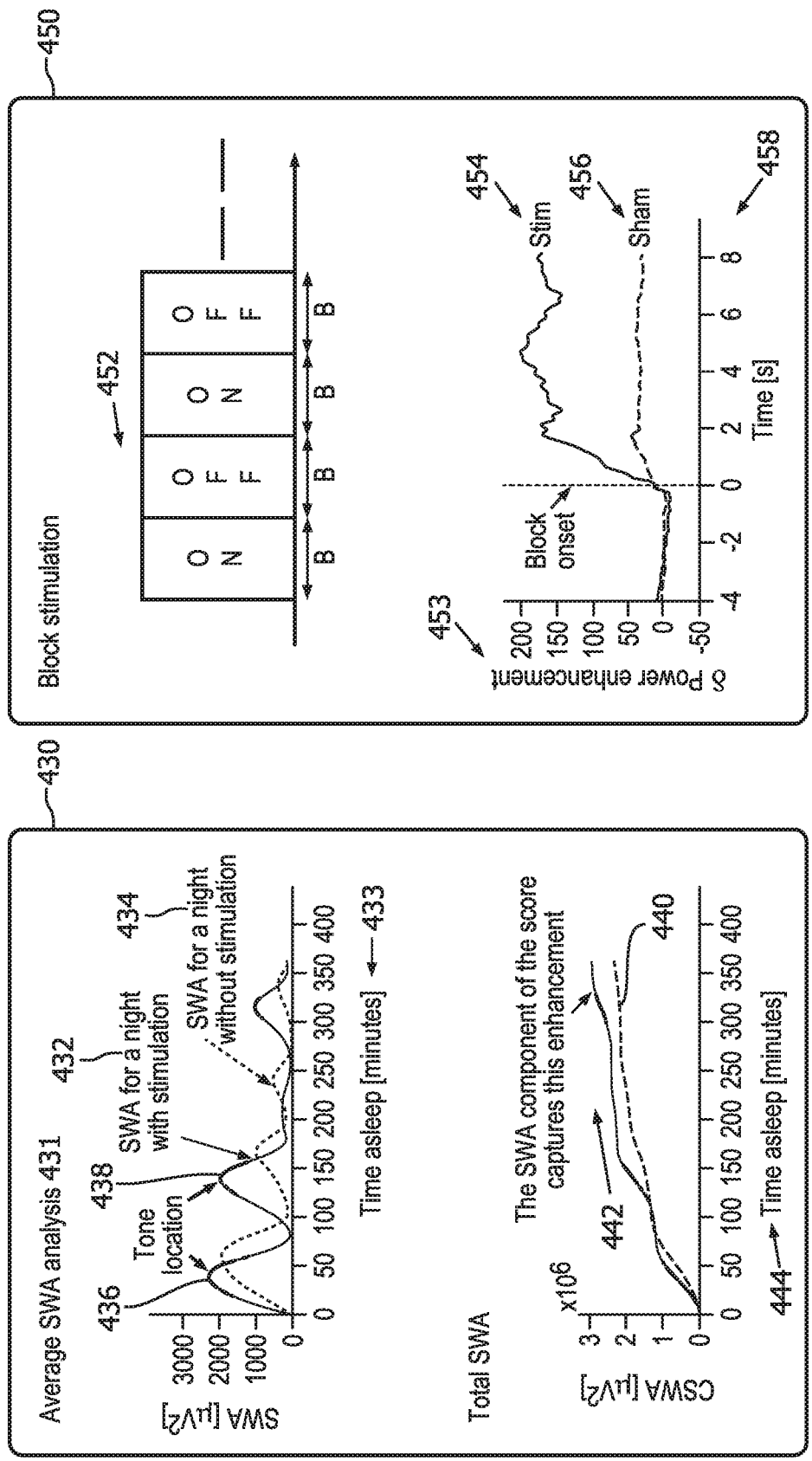

Field 430 of FIG. 4B illustrates analyzing 431 average SWA in a user (e.g., user 12) for a night 433 (time asleep) with stimulation 432 and a night 433 without stimulation 434. As shown in Field 430, SWA varies cyclically throughout night 433 with SWA peaks 436 for the night with stimulation exceeding the SWA peaks 438 for the night without stimulation. Total SWA 440 is also shown in Field 430. Total SWA 440 is a summation of SWA in a user and increases 442 throughout a given sleep session 444. Field 450 illustrates ON and OFF stimulation blocks 452 and resulting SWA 453 in a user for stimulation 454 (stimulation provided) and sham 456 (no stimulation provided) sleep sessions 458, where "B" is a duration (e.g., in seconds) of the ON/OFF blocks and "T" is a number of tones in the ON block.

Returning to FIG. 1, in some embodiments, quantification component 40 is configured to cause sensory stimulator 16 to adjust the sensory stimulation provided to user 12. In some embodiments, this adjustment is instead of and/or in addition to the adjustments made by stimulation strategy component 38. In some embodiments, quantification component 40 is configured to cause sensory stimulator 16 to adjust the sensory stimulation provided to the user based on the effect of the sensory stimulation provided to the user determined using the quantification method associated with the stimulation strategy and the target cognitive domain and/or other information. For example, in some embodiments, quantification component 40 may determine a SWA change in user 12 during ON and OFF blocks of sensory stimulation during the sleep session, average SWA in user 12 during the sleep session, or total SWA in user 12 during deep sleep in the sleep session, and compare the determination to a corresponding threshold. Responsive to the determining breaching (or not breaching) the corresponding threshold, quantification component 40 may cause sensory stimulator 16 to adjust an intensity, timing, interval, frequency, and/or other parameters of the stimulation provided to user 12. These adjustments may be configured to increase and/or decrease SWA in user 12 and/or enhance (and/or further enhance after the adjustment) a target cognitive domain in user 12.

In some embodiments, quantification component 40 is configured to adjust the sensory stimulation provided to user 12 based on a difference between a desired cognitive performance and an actual cognitive performance in user 12. In some embodiments, this difference may be determined based on measurements made before and/or after one or more sleep sessions, and/or at other times. For example, in some embodiments, quantification component 40 may determine a level (e.g., absolute, not relative) of cognitive performance in user 12. In some embodiments, quantification component 40 may determine a (e.g., relative) difference in the cognitive performance of user 12 before and after one or more sleeps sessions. Quantification component 40 may compare the (e.g., relative or absolute) cognitive performance of user 12 to a corresponding cognitive performance threshold. Responsive to the cognitive performance breaching (or not breaching) the corresponding threshold, quantification component 40 may cause sensory stimulator 16 to adjust an intensity, timing, interval, frequency, and/or other parameters of the stimulation provided to user 12. These adjustments may be configured to increase and/or decrease SWA in user 12 and/or enhance (and/or further enhance after the adjustment) a target cognitive domain in user 12.

Figure 5:
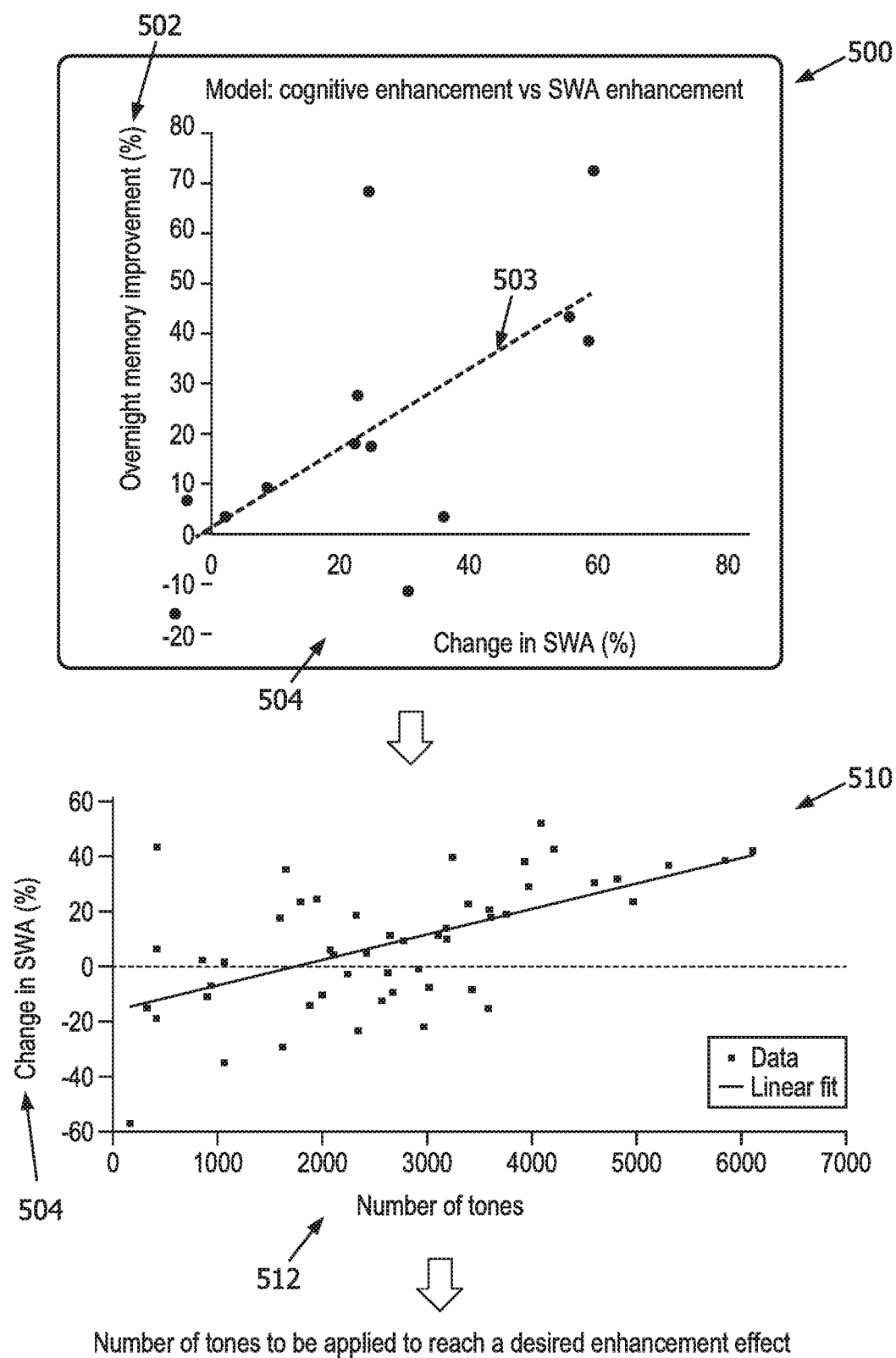
FIG. 5 illustrates an example of adjusting parameters of the sensory stimulation provided to a user based on a difference between a desired cognitive performance and an actual cognitive performance.

FIG. 5 illustrates an example of adjusting parameters of the sensory stimulation provided to a user (e.g., user 12) based on a difference between a desired cognitive performance and an actual cognitive performance. This difference may be determined, for example, based on measurements made before and/or after a sleep session, and/or at other times. For example, a user may be asked questions, shown images, required to write, perform tasks, etc. as part of such an evaluation. As shown in Field 500, cognitive enhancement 502 positively correlates 503 with a change in SWA 504 in a user during a sleep session. The change in SWA 504 in a user during a sleep session can be measured as and adjusted as described herein by adjusting the sensory stimulation provided to a user. As shown in Field 510 of FIG. 5, for auditory sensory stimulation, increasing the number of tones 512 increases the change in SWA 504. This means that changing the number of tones provided to a user will change the users cognitive performance, and a user's cognitive performance can be changed by a specific amount by providing a corresponding number of tones to the user during a sleep session. This example is not intended to be limiting. System 10 (FIG. 1) is configured such that, given a targeted cognitive domain and a desired enhancement effect, the corresponding SWA change can be estimated through a correlational model similar to and/or the same as the one shown in FIG. 5. The latter can be related to any stimulation parameter (e.g., the number of tones and/or other parameters).

With respect to FIG. 5 (and/or one or more components of system 10 shown in FIG. 1 and described herein), sensory stimulation has a differentiated effect on SWA depending on the EEG location (e.g., frontal, central, or occipital) where the signal is acquired. Thus, in addition to the associations with the stimulation strategies and/or SWA quantification methods, the target cognitive domains may also be associated with EEG acquisition sites.

Figure 6:
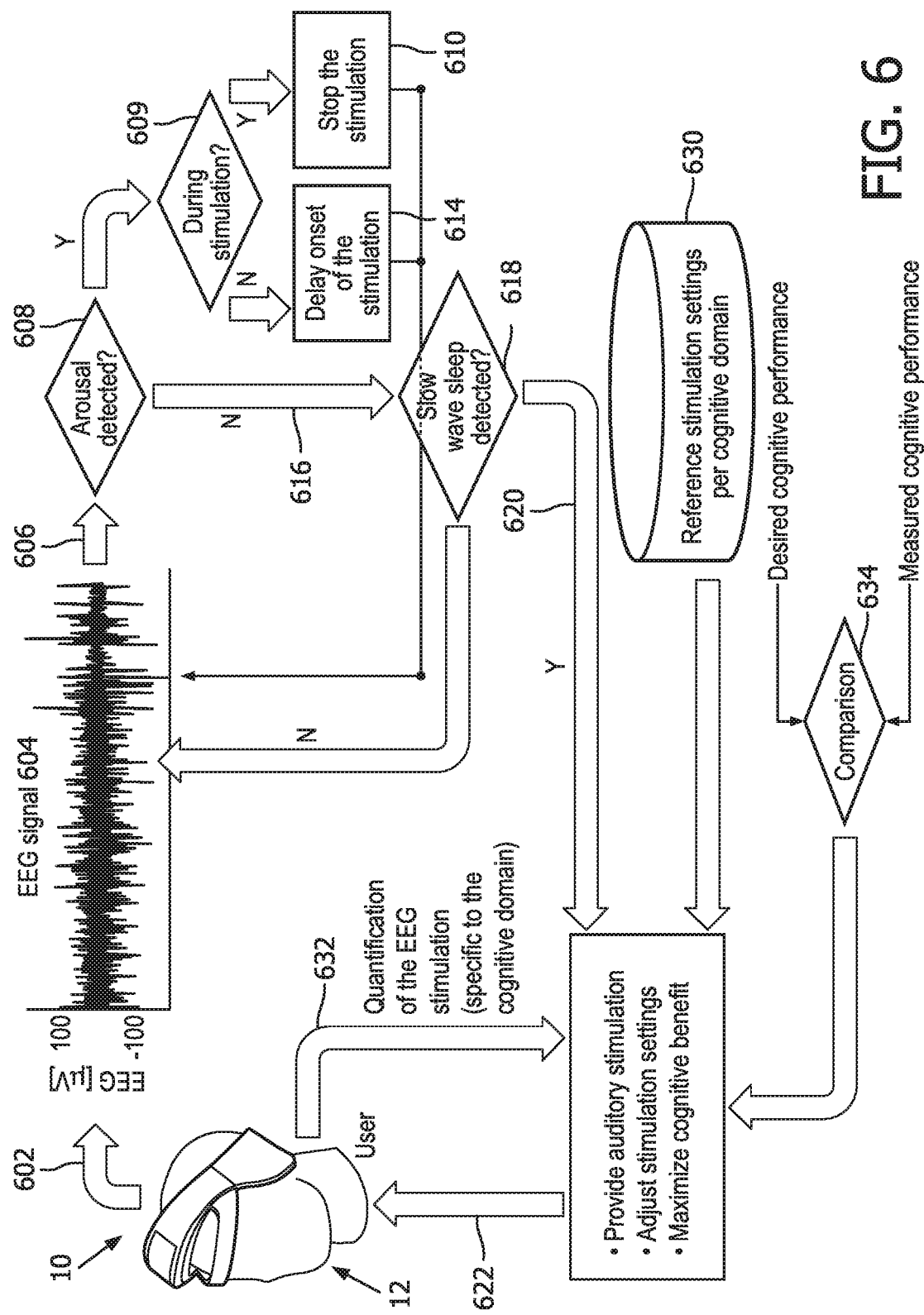
FIG. 6 illustrates operations performed by system.

An example illustration of operations 600 performed by system 10 (also shown in FIG. 1) is shown in FIG. 6. As shown in FIG. 6, EEG electrodes generate 602 an EEG signal 604. The presence of EEG patterns (high power in the alpha 8-12 Hz and/or beta 15-30 Hz bands) indicative of (micro) arousals is evaluated 606 by system 10. If arousal-like activity is detected 608 in the EEG during stimulation 609, stimulation is controlled to stop 610. If the arousal-like activity is detected 608 outside the stimulation period, the onset of the next stimulation is delayed 614. If no arousal-like activity is detected 616, then system 10 attempts to detect 618 deep sleep based on the power in the SWA band (0.5 to 4 Hz), the temporal density of detected slow-waves, and/or other information. Responsive to detection of sufficiently deep sleep 620, system 10 is configured such that auditory (as in the example shown in FIG. 6 but this is not intended to be limiting) stimulation is delivered 622. System 10 is configured such that the stimulation strategy and quantification method are determined 630 based on the target cognitive domain and/or other information. System 10 is configured such that the stimulation received by user 12 is adjusted 632 based on the quantification of the EEG (specific to the cognitive domain), based on a comparison 634 of a desired cognitive performance with a measured cognitive performance, and/or other information.

Returning to FIG. 1, electronic storage 22 comprises electronic storage media that electronically stores information. The electronic storage media of electronic storage 22 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), cloud storage, and/or other electronically readable storage media. Electronic storage 22 may store software algorithms, information determined by processor 20, information received via user interface 24 and/or external computing systems (e.g., external resources 26), and/or other information that enables system 10 to function as described herein. Electronic storage 22 may be (in whole or in part) a separate component within system 10, or electronic storage 22 may be provided (in whole or in part) integrally with one or more other components of system 10 (e.g., processor 20).

User interface 24 is configured to provide an interface between system 10 and user 12, and/or other users through which user 12 and/or other users may provide information to and receive information from system 10. This enables data, cues, results, and/or instructions and any other communicable items, collectively referred to as "information," to be communicated between a user (e.g., user 12) and one or more of sensory stimulator 16, sensor 18, processor 20, and/or other components of system 10. For example, an EEG may be displayed to a caregiver via user interface 24. As another example, user interface 24 may be and/or be included in a computing device such as a desktop computer, a laptop computer, a smartphone, a tablet computer, and/or other computing devices. Such computing devices may run one or more electronic applications having graphical user interfaces configured to provide information to and/or receive information from users.

Examples of interface devices suitable for inclusion in user interface 24 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, user interface 24 comprises a plurality of separate interfaces. In some embodiments, user interface 24 comprises at least one interface that is provided integrally with processor 20 and/or other components of system 10. In some embodiments, user interface 24 is configured to communicate wirelessly with processor 20 and/or other components of system 10.

It is to be understood that other communication techniques, either hard-wired or wireless, are also contemplated by the present disclosure as user interface 24. For example, the present disclosure contemplates that user interface 24 may be integrated with a removable storage interface provided by electronic storage 22. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 24 comprise, but are not limited to, an RS-232 port, RF link, an IR link, modem (telephone, cable or other). In short, any technique for communicating information with system 10 is contemplated by the present disclosure as user interface 24.

External resources 26 include sources of information (e.g., databases, websites, etc.), external entities participating with system 10 (e.g., a medical records system of a health care provider), medical and/or other equipment (e.g., lamps and/or other lighting devices, sound systems, audio and/or visual recording devices, etc.) configured to communicate with and/or be controlled by system 10, one or more servers outside of system 10, a network (e.g., the internet), electronic storage, equipment related to Wi-Fi technology, equipment related to Bluetooth® technology, data entry devices, sensors, scanners, computing devices associated with individual users, and/or other resources. In some implementations, some or all of the functionality attributed herein to external resources 26 may be provided by resources included in system 10. External resources 26 may be configured to communicate with processor 20, user interface 24, sensor 18, electronic storage 22, sensory stimulator 16, and/or other components of system 10 via wired and/or wireless connections, via a network (e.g., a local area network and/or the internet), via cellular technology, via Wi-Fi technology, and/or via other resources.

Figure 7:
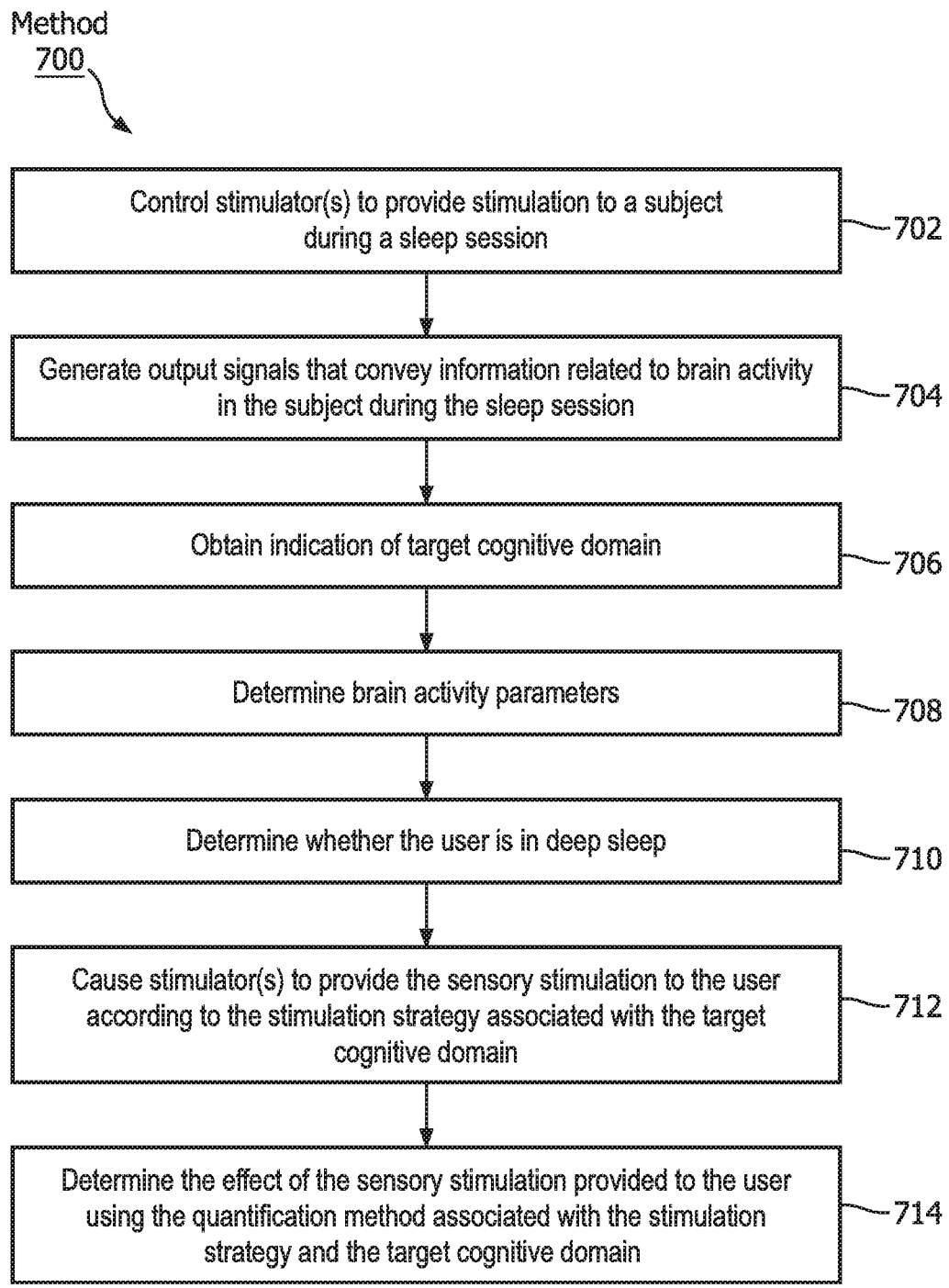
FIG. 7 illustrates a method for delivering sensory stimulation to a user to enhance a cognitive domain in the user.

FIG. 7 illustrates method 700 for delivering sensory stimulation to a user to enhance a target cognitive domain in the user during a sleep session with a sensory stimulation system. The system comprises one or more sensory stimulators, one or more sensors, one or more hardware processors configured by machine readable instructions, and/or other components. The one or more hardware processors are configured to execute computer program components. The computer program components comprise a control component, a parameter component, a slow wave activity component, a cognitive domain component, a stimulation strategy component, a quantification component, and/or other components. The operations of method 700 presented below are intended to be illustrative. In some embodiments, method 700 may be accomplished with one or more additional operations not described, and/or without one or more of the operations discussed. Additionally, the order in which the operations of method 700 are illustrated in FIG. 7 and described below is not intended to be limiting.

In some embodiments, method 700 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 700 in response to instructions stored electronically on an electronic storage medium. The one or more processing devices may include one or more devices configured through hardware, firmware, and/or software to be specifically designed for execution of one or more of the operations of method 700.

At an operation 702, the one or more stimulators are controlled to provide stimulation to a user during sleep sessions. In some embodiments, the one or more stimulators comprise a tone generator and/or other stimulators. In some embodiments, the sensory stimulation comprises one or more of auditory stimulation, visual stimulation, or somatosensory stimulation. In some embodiments, operation 702 is performed by a processor component the same as or similar to control component 30 (shown in FIG. 1 and described herein).

At an operation 704, output signals conveying information related to brain activity in the user are generated. In some embodiments, the one or more sensors comprise electroencephalogram (EEG) sensors and/or other sensors configured to generate output signals conveying information related to slow wave activity in the user. In some embodiments, the one or more sensors comprise one or more of an EEG electrode, an electrooculogram (EOG) electrode, an actigraphy sensor, an electrocardiogram (EKG) electrode, a respiration sensor, a pressure sensor, a vital signs camera, a photoplethysmogram (PPG) sensor, or a functional near infra-red sensor (fNIR). In some embodiments, operation 704 is performed by one or more sensors the same as or similar to sensors 18 (shown in FIG. 1 and described herein).

At an operation 706, an indication of a target cognitive domain is obtained. In some embodiments, the target cognitive domain comprises one or more of memory consolidation, vigilance, verbal fluency, sleepiness, memory encoding, learning efficiency, and/or other cognitive domains. In some embodiments, the target cognitive domain is associated with a stimulation strategy and a quantification method for quantifying an effect of sensory stimulation delivered according to the stimulation strategy. The stimulation strategy may indicate a pattern, a timing, and/or an intensity of the sensory stimulation provided to the user. In some embodiments, operation 706 is performed by a processor component the same as or similar to cognitive domain component 36 (shown in FIG. 1 and described herein).

At an operation 708, brain activity parameters are determined. The brain activity parameters are determined based on the output signals and/or other information. In some embodiments, operation 708 is performed by a processor component the same as or similar to parameter component 32 (shown in FIG. 1 and described herein).

At an operation 710, a determination of whether a user is in sufficiently deep sleep is made. The determination is made based on the brain activity parameters and/or other information. In some embodiments, operation 710 is performed by a processor component the same as or similar to slow wave activity component 34 (shown in FIG. 1 and described herein).

At an operation 712, the stimulators are caused to provide the sensory stimulation to the user according to the stimulation strategy associated with the target cognitive domain. The stimulators are caused to provide the sensory stimulation according to the stimulation strategy associated with the target cognitive domain responsive to the one or more brain activity parameters indicating the user is in sufficiently deep sleep. In some embodiments, the memory consolidation target cognitive domain is associated with a block stimulation strategy. In some embodiments, the vigilance, verbal fluency, and sleepiness target cognitive domains are associated with continuous stimulation strategies. In some embodiments, operation 712 is performed by a processor component the same as or similar to stimulation strategy component 38 (shown in FIG. 1 and described herein).

At an operation 714, the effect of the sensory stimulation provided to the user is determined using the quantification method associated with the stimulation strategy and the target cognitive domain. In some embodiments, the memory consolidation target cognitive domain is associated with a quantification method comprising determining a slow wave activity change in the user during "on" and "off" blocks of sensory stimulation during the sleep session. In some embodiments, the vigilance target cognitive domain is associated with a quantification method comprising determining average slow wave activity across NREM sleep in the user during the sleep session. In some embodiments, the verbal fluency target cognitive domain is associated with a quantification method comprising determining total slow wave activity in the user during deep sleep in the sleep session. In some embodiments, the sleepiness target cognitive domain is associated with a quantification method comprising determining the average slow wave activity in the user during the sleep session.

In some embodiments, operation 714 includes adjusting the sensory stimulation provided to the user based on one or both of the effect of the sensory stimulation provided to the user using the quantification method associated with the stimulation strategy and the target cognitive domain; and a difference between a desired cognitive performance and an actual cognitive performance measured after the sleep session. In some embodiments, operation 714 is performed by a processor component the same as or similar to quantification component 40 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to deliver sensory stimulation to a user to enhance a target cognitive domain in the user during a sleep session, the system comprising:
   one or more sensory stimulators configured to provide sensory stimulation to the user during the sleep session;
   one or more sensors configured to generate output signals conveying information related to brain activity of the user during the sleep session; and
   one or more hardware processors coupled to the one or more sensory stimulators and the one or more sensors, the one or more hardware processors configured by machine readable instructions to:
      obtain an indication of the target cognitive domain for enhancement in the user, the target cognitive domain associated with a stimulation strategy and a quantification method for quantifying an effect of sensory stimulation delivered according to the stimulation strategy, the stimulation strategy indicating a pattern, a timing, and/or an intensity of the sensory stimulation provided to the user;
      determine one or more brain activity parameters of the user during the sleep session based on the output signals;
      determine whether the one or more brain activity parameters indicate the user is in sufficiently deep sleep; and
      responsive to the one or more brain activity parameters indicating the user is in sufficiently deep sleep, cause the one or more sensory stimulators to provide the sensory stimulation to the user according to the stimulation strategy associated with the target cognitive domain, wherein the one or more hardware processors are configured to apply different stimulation strategies depending on which cognitive domain is targeted, and determine the effect of the sensory stimulation provided to the user using the quantification method associated with the stimulation strategy and the target cognitive domain,
   wherein the one or more hardware processors are configured by machine readable instructions to cause the one or more sensory stimulators to provide the sensory stimulation to the user according to the stimulation strategy associated with memory consolidation, vigilance, verbal fluency, and sleepiness target cognitive domains, and wherein the one or more hardware processors are configured by machine readable instructions to determine the effect of the sensory stimulation provided to the user using the quantification method associated with memory consolidation, vigilance, verbal fluency, and sleepiness target cognitive domains,
   wherein the stimulation strategy associated with the memory consolidation target cognitive domain includes a block stimulation strategy and the stimulation strategies associated with the vigilance, verbal fluency, and sleepiness target cognitive domains each include a continuous stimulation strategy,
   wherein the quantification method associated with the memory consolidation target cognitive domain includes determining a slow wave activity change in the user during "on" and "off" blocks of sensory stimulation during the sleep session, the quantification method associated with the vigilance target cognitive domain includes determining average slow wave activity across NREM sleep in the user during the sleep session, the quantification method associated with the verbal fluency target cognitive domain includes determining total slow wave activity in the user during deep sleep in the sleep session, and the quantification method associated with the sleepiness target cognitive domain includes determining the average slow wave activity in the user during the sleep session.

2. The system of claim 1, wherein the one or more hardware processors are further configured to adjust the sensory stimulation provided to the user based on one or both of:
   the effect of the sensory stimulation provided to the user using the quantification method associated with the stimulation strategy and the target cognitive domain; and
   a difference between a desired cognitive performance and an actual cognitive performance measured after the sleep session.

3. The system of claim 1, wherein the one or more sensory stimulators are configured such that the sensory stimulation comprises one or more of auditory stimulation, visual stimulation, or somatosensory stimulation.

4. The system of claim 1, wherein the one or more sensors comprise one or more of an electroencephalogram (EEG) electrode, an electrooculogram (EOG) electrode, an actigraphy sensor, an electrocardiogram (EKG) electrode, a respiration sensor, a pressure sensor, a vital signs camera, a photoplethysmogram (PPG) sensor, or a functional near infra-red (fNIR) sensor.

5. A method for delivering sensory stimulation to a user to enhance a target cognitive domain in the user during a sleep session with a sensory stimulation system, the system comprising one or more sensory stimulators, one or more sensors, and one or more hardware processors configured by machine readable instructions, the method comprising:
providing, with the one or more sensory stimulators, sensory stimulation to the user during the sleep session;
generating, with the one or more sensors, output signals conveying information related to brain activity of the user during the sleep session;
obtaining, with the one or more hardware processors, an indication of the target cognitive domain for enhancement in the user, the target cognitive domain associated with a stimulation strategy and a quantification method for quantifying an effect of sensory stimulation delivered according to the stimulation strategy, the stimulation strategy indicating a pattern, a timing, and/or an intensity of the sensory stimulation provided to the user;
determining, with the one or more hardware processors, one or more brain activity parameters of the user during the sleep session based on the output signals;
determining, with the one or more hardware processors, whether the one or more brain activity parameters indicate the user is in sufficiently deep sleep; and
responsive to the one or more brain activity parameters indicating the user is in sufficiently deep sleep, causing, with the one or more hardware processors, the one or more sensory stimulators to provide the sensory stimulation to the user according to the stimulation strategy associated with the target cognitive domain, and applying different stimulation strategies depending on which cognitive domain is targeted, and determining, with the one or more hardware processors, the effect of the sensory stimulation provided to the user using the quantification method associated with the stimulation strategy and the target cognitive domain,
wherein the one or more hardware processors are configured to cause the one or more sensory stimulators to provide the sensory stimulation to the user according to the stimulation strategy associated with memory consolidation, vigilance, verbal fluency, and sleepiness target cognitive domains, and wherein the one or more hardware processors are configured to determine the effect of the sensory stimulation provided to the user using the quantification method associated with memory consolidation, vigilance, verbal fluency, and sleepiness target cognitive domains,
wherein the stimulation strategy associated with the memory consolidation target cognitive domain includes a block stimulation strategy and the stimulation strategies associated with the vigilance, verbal fluency, and sleepiness target cognitive domains each include a continuous stimulation strategy,
wherein the quantification method associated with the memory consolidation target cognitive domain includes determining a slow wave activity change in the user during "on" and "off" blocks of sensory stimulation during the sleep session, the quantification method associated with the vigilance target cognitive domain includes determining average slow wave activity across NREM sleep in the user during the sleep session, the quantification method associated with the verbal fluency target cognitive domain includes determining total slow wave activity in the user during deep sleep in the sleep session, and the quantification method associated with the sleepiness target cognitive domain includes determining the average slow wave activity in the user during the sleep session.

6. The method of claim 5, further comprising adjusting, with the one or more hardware processors, the sensory stimulation provided to the user based on one or both of:
the effect of the sensory stimulation provided to the user using the quantification method associated with the stimulation strategy and the target cognitive domain; and
a difference between a desired cognitive performance and an actual cognitive performance measured after the sleep session.

7. The method of claim 5, wherein the sensory stimulation comprises one or more of auditory stimulation, visual stimulation, or somatosensory stimulation.

8. The method of claim 5, wherein the one or more sensors comprise one or more of an electroencephalogram (EEG) electrode, an electrooculogram (EOG) electrode, an actigraphy sensor, an electrocardiogram (EKG) electrode, a respiration sensor, a pressure sensor, a vital signs camera, a photoplethysmogram (PPG) sensor, or a functional near infra-red (fNIR) sensor.

9. A system for delivering sensory stimulation to a user to enhance a target cognitive domain in the user during a sleep session, the system comprising:
means for providing sensory stimulation to the user during the sleep session;
means for generating output signals conveying information related to brain activity of the user during the sleep session;
means for obtaining an indication of the target cognitive domain for enhancement in the user, the target cognitive domain associated with a stimulation strategy and a quantification method for quantifying an effect of sensory stimulation delivered according to the stimulation strategy, the stimulation strategy indicating a pattern, a timing, and/or an intensity of the sensory stimulation provided to the user;
means for determining one or more brain activity parameters of the user during the sleep session based on the output signals;
means for determining whether the one or more brain activity parameters indicate the user is in sufficiently deep sleep; and
means for, responsive to the one or more brain activity parameters indicating the user is in sufficiently deep sleep, causing the one or more sensory stimulators to provide the sensory stimulation to the user according to the stimulation strategy associated with the target cognitive domain, and applying different stimulation strategies depending on which cognitive domain is targeted, and determining the effect of the sensory stimulation provided to the user using the quantification method associated with the stimulation strategy and the target cognitive domain, wherein the means for causing the one or more sensory stimulators to provide the sensory stimulation to the user are configured to cause the one or more sensory stimulators to provide the sensory stimulation to the user according to the stimulation strategy associated with memory consolidation, vigilance, verbal fluency, and sleepiness target cognitive domains, and are configured by machine readable instructions to determine the effect of the sensory stimulation provided to the user using the quantification method associated with memory consolidation, vigilance, verbal fluency, and sleepiness target cognitive domains, wherein the stimulation strategy associated with the memory consolidation target cognitive domain includes a block stimulation strategy and the stimulation strategies associated with the vigilance, verbal fluency, and sleepiness target cognitive domains each include a continuous stimulation strategy, wherein the quantification method associated with the memory consolidation target cognitive domain includes determining a slow wave activity change in the user during "on" and "off" blocks of sensory stimulation during the sleep session, the quantification method associated with the vigilance target cognitive domain includes determining average slow wave activity across NREM sleep in the user during the sleep session, the quantification method associated with the verbal fluency target cognitive domain includes determining total slow wave activity in the user during deep sleep in the sleep session, and the quantification method associated with the sleepiness target cognitive domain includes determining the average slow wave activity in the user during the sleep session.

10. The system of claim 9, further comprising means for adjusting the sensory stimulation provided to the user based on one or both of:
   the effect of the sensory stimulation provided to the user using the quantification method associated with the stimulation strategy and the target cognitive domain; and
   a difference between a desired cognitive performance and an actual cognitive performance measured after the sleep session.

11. The system of claim 9, wherein the sensory stimulation comprises one or more of auditory stimulation, visual stimulation, or somatosensory stimulation.

12. The system of claim 9, wherein the means for generating output signals comprise one or more of an electroencephalogram (EEG) electrode, an electrooculogram (EOG) electrode, an actigraphy sensor, an electrocardiogram (EKG) electrode, a respiration sensor, a pressure sensor, a vital signs camera, a photoplethysmogram (PPG) sensor, or a functional near infra-red (fNIR) sensor.

* * * * *